United States Patent [19]

van Duyn

[11] Patent Number: Plant 6,611

[45] Date of Patent: Feb. 14, 1989

[54] ALSTROEMERIA NAMED SWEETHEART

[75] Inventor: Cornelis van Duyn, NA Rijnsburg, Netherlands

[73] Assignee: Groot Associates II, Irvine, Calif.

[21] Appl. No.: 57,238

[22] Filed: Jun. 1, 1987

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Jackson & Jones

[57] ABSTRACT

A new Alstroemeria variety characterized by the brightly colored blossoms, the petals of which are pink, with white wings and a yellow-white striped heart which is sometimes bearded. The plant is late in flowering with relatively short stems.

1 Drawing Sheet

BACKGROUND OF THE NEW PLANT

This new Alstroemeria originated as a seedling selected from individual members of breeding stock maintained at Rijnsburg, Holland. The particular seedling was selected by me in 1984 for propagation and testing because of its blossoms produced on upright compact stems. Specifically, the inner and outer petals have pink central areas with white wings and a yellow-white striped heart and are sometimes bearded. The inner petals have well defined longitudinal streaks or flecks of dark pink while the outer petals are limited to pink central areas with the white wings. The selected plant was propagated by me at Rijnsburg, Holland through several generations of root divisions to establish that its distinctive characteristics hold true from generation to generation and appear to be firmly fixed.

Breeding efforts commenced in 1980 and propagation is currently being carried out at Rijnsburg, Holland. The nearest variety is the Alstroemeria called Jacqueline and my new variety, Sweetheart, differs from the Jacqueline variety in that (1) the flowers are more brightly colored, (2) the flowers are also bearded with a brighter color, (3) the flower size is smaller, (4) the plant is later flowering and (5) the flower stems are shorter.

DESCRIPTION OF THE DRAWING

This new variety of the Alstroemeria plant is illustrated by the accompanying photograph which shows a blooming umbel of the plant with buds and flowers in various stages of opening.

DESCRIPTION OF THE NEW PLANT

The following is a detailed description of my new Alstroemeria plant with color designations according to The National Bureau of Standards, Standard Reference Material, #2107, comprising the ISCC-NBS Centroid Color Charts and NBS Special Publication, #440.

THE PLANT

Origin: Seedling.
Parentage: Seed parent.
Classification: Alstroemeria Butterfly-type.
Form: A generally erect bush having an upright stalk with flower-bearing branches in simple umbel arrangement at its top.
Height: About 1.05 meters.
Growth: Upright and vigorous.

Root stock: Tuberous.
Foliage:
- *Quantity.*—Abundant.
- *Number of leaves.*—About 15 per stem.
- *Size of leaf.*—About 12×3.1 cm.
- *Shape of leaf.*—Parallel venation.
- *Texture.*—Smooth.
- *Color.*—Upper side: Green. Under side: Green.

THE BUD

Form: Long, pear shaped.
Size: Large.
- *Diameter.*—About 1.0 cm.
- *Length.*—About 3.0 cm.

Peduncle:
- *Length.*—About 10 cm.
- *Texture.*—Smooth.
- *Form.*—Erect.

THE FLOWER

Blooming habit: Profusely during late season in Spring.
Flower size: Medium.
- *Diameter.*—About 4 cm.
- *Depth.*—About 5.5 cm.

Borne: Terminal clusters.
Shape: Generally cup shaped with petal tips curling outwardly.
Petalage:
- *Number of petals.*—Six.
- *Arrangement.*—Two concentric circles of three.
- *Form.*—Broad ovate.
- *Texture.*—Soft.
- *Appearance.*—Velvety.

Color:
- *Outer petals.*—Moderate pinkish red (No. 255) with light pink (No. 250) fading to white (No. 263) margins.
- *Inner petals.*—Moderate pinkish red (No. 255) with white (No. 263) margins and light yellowish green (No. 119) heart. The inner petals have numerous generally longitudinal stripes or flecks of deep purplish red (No. 260).

Persistence: The flowers hang on and dry.
Main stem or stalk:
- *Length.*—About 10 cm.
- *Color.*—Green.
- *Character.*—Strong and upright.

Lasting quality of flower: About three weeks. As a cut flower, about 10–14 days.

REPRODUCTIVE ORGANS

Stamens:

*Number.*—Six.

*Arrangement.*—One opposite each petal.

Anthers:

*Size.*—About 0.7 cm×0.2 cm.

*Color.*—Yellowish green (No. 122).

Filaments:

*Length.*—About 3 cm.

*Color.*—Light purplish pink (No. 249).

*Pollen.*—Purplish grey.

Pistils:

*Number.*—One.

*Styles.*—Length: About 3 cm. Color: Light pink.

Fruit:

*Shape.*—Round.

*Color.*—Light Brown.

This plant is particularly noted for the distinctive coloration of its flowers, which coloration is more brightly colored and does not clearly resemble that of any other Alstroemeria plant previously known to me. The deep purplish red flecks on the moderate purplish red (central) and white margins with the light orange yellow on the inner petals and moderate purplish pink with white margins on the outer petals make this plant an attractive addition to the alstroemeria family.

I claim:

1. A new and distinctive Alstroemeria cultivar, substantially as herein shown and described, characterized by the distinctive coloration of its medium and profusely blooming flowers.

* * * * *

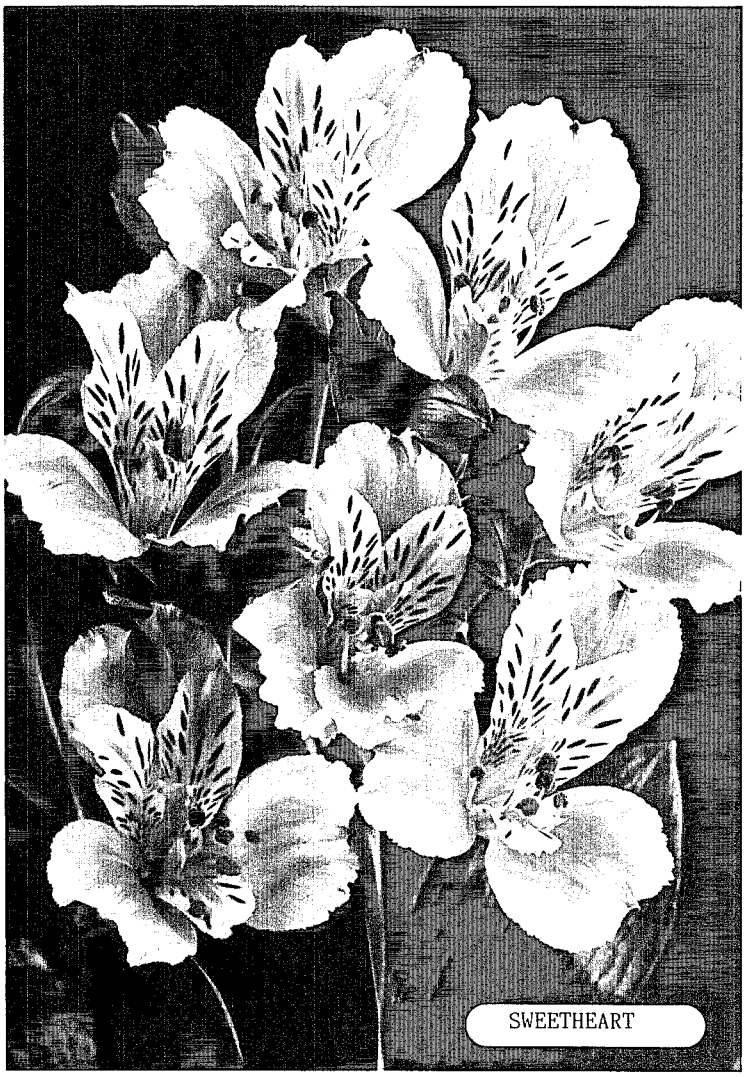
SWEETHEART